United States Patent
Wu et al.

(10) Patent No.: US 10,268,915 B2
(45) Date of Patent: Apr. 23, 2019

(54) REAL-TIME COLLIMATION AND ROI-FILTER POSITIONING IN X-RAY IMAGING VIA AUTOMATIC DETECTION OF THE LANDMARKS OF INTEREST

(71) Applicant: Siemens Healthcare GmbH, Erlangen (DE)

(72) Inventors: Wen Wu, Kirkland, WA (US); Terrence Chen, Princeton, NJ (US); Anton Nekovar, Neunkirchen (DE); Martin Ostermeier, Buckenhof (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 2 days.

(21) Appl. No.: 15/574,203

(22) PCT Filed: Jun. 9, 2015

(86) PCT No.: PCT/US2015/034792
§ 371 (c)(1),
(2) Date: Nov. 15, 2017

(87) PCT Pub. No.: WO2016/200370
PCT Pub. Date: Dec. 15, 2016

(65) Prior Publication Data
US 2018/0129896 A1 May 10, 2018

(51) Int. Cl.
*G06K 9/00* (2006.01)
*G06K 9/32* (2006.01)
(Continued)

(52) U.S. Cl.
CPC .............. *G06K 9/3233* (2013.01); *A61B 6/06* (2013.01); *A61B 6/12* (2013.01); *A61B 6/469* (2013.01);
(Continued)

(58) Field of Classification Search
CPC .. A61B 6/06; A61B 6/542; A61B 6/12; A61B 6/545; A61B 6/487; A61B 6/469;
(Continued)

(56) References Cited

U.S. PATENT DOCUMENTS

| 5,278,887 A | 1/1994 | Chiu et al. | |
| 5,651,043 A * | 7/1997 | Tsuyuki | A61N 5/1042 378/65 |

(Continued)

FOREIGN PATENT DOCUMENTS

WO 2014033573 A1 3/2014

OTHER PUBLICATIONS

International Search Report dated Dec. 9, 2015 for Corresponding Application No. PCT/US2015/034792.
(Continued)

*Primary Examiner* — Li Liu (57) ABSTRACT

A method for real-time collimation and ROI-filter positioning in X-ray imaging in interventional procedures includes acquiring an image of a region-of-interest (ROI) at a beginning of a medical intervention procedure on a subject, classifying the image based on low-level features in the image to determine a type of procedure being performed, determining a list of landmarks in the image from the type of procedure being performed, and loading a pre-trained landmark model for each landmark in the list of landmarks, where landmarks include anatomical structures of the subject and medical devices being used in the medical intervention procedure, and computing collimator settings of an
(Continued)

X-ray imaging device from ROI filter margins and bounding boxes of the landmarks calculated using the landmark models.

24 Claims, 5 Drawing Sheets

(51) Int. Cl.
*A61B 6/06* (2006.01)
*A61B 6/12* (2006.01)
*A61B 6/00* (2006.01)

(52) U.S. Cl.
CPC .............. *A61B 6/487* (2013.01); *A61B 6/504* (2013.01); *A61B 6/5211* (2013.01); *A61B 6/545* (2013.01); *G06K 2009/3225* (2013.01); *G06K 2209/057* (2013.01)

(58) Field of Classification Search
CPC ... A61B 5/0037; A61B 6/54; A61B 2090/376; A61B 5/061; A61B 90/37; G06K 2009/3225; G06K 2209/057; G06K 9/3233
See application file for complete search history.

(56) References Cited

U.S. PATENT DOCUMENTS

| | | | |
|---|---|---|---|
| 6,055,295 A | 4/2000 | Murthy et al. | |
| 6,530,874 B2 | 3/2003 | Uematsu et al. | |
| 7,340,033 B2 | 3/2008 | Mollus et al. | |
| 8,311,308 B2 | 11/2012 | Chen et al. | |
| 8,423,121 B2 | 4/2013 | Want et al. | |
| 8,548,213 B2 | 10/2013 | Wels et al. | |
| 8,565,859 B2 | 10/2013 | Want et al. | |
| 2011/0182492 A1* | 7/2011 | Grass | A61B 6/4441 382/131 |
| 2012/0070046 A1 | 3/2012 | Wu et al. | |
| 2013/0072773 A1 | 3/2013 | Wu et al. | |
| 2013/0245429 A1 | 9/2013 | Zhang et al. | |
| 2013/0272504 A1* | 10/2013 | Deutsch | G21K 1/04 378/150 |
| 2013/0343631 A1 | 12/2013 | Florent et al. | |
| 2014/0169525 A1* | 6/2014 | Shimizu | A61B 6/542 378/62 |
| 2015/0228071 A1* | 8/2015 | Jockel | A61B 6/08 382/132 |
| 2015/0245804 A1* | 9/2015 | Kieft | A61B 6/06 378/147 |
| 2015/0265226 A1* | 9/2015 | Jackson | A61B 6/06 378/16 |
| 2016/0007950 A1* | 1/2016 | Lim | A61B 6/08 378/42 |
| 2016/0029981 A1* | 2/2016 | Van Dijk | A61B 6/06 600/424 |

OTHER PUBLICATIONS

Wen Wu, et al., "Learning-based hypothesis fusion for robust catheter tracking in 2D X-ray flurorscopy", Computer Vision and Pattern Recognition (CVPR), 2011 IEEE Conference on, IEEE, Jun. 20, 2011. pp. 1097-1104.

* cited by examiner

REAL-TIME COLLIMATION AND ROI-FILTER POSITIONING IN X-RAY IMAGING VIA AUTOMATIC DETECTION OF THE LANDMARKS OF INTEREST

TECHNICAL FIELD

This disclosure is directed to methods for real-time collimation and region-of-interest (ROI)-filter positioning in X-ray imaging in interventional procedures via automatic detection and tracking of landmarks of interest.

DISCUSSION OF THE RELATED ART

Most interventional procedures today use X-ray fluoroscopy for imaging and guidance. These interventional procedures are normally performed with computerized X-ray imaging systems. The system is called a monoplane system if it uses only one X-ray imaging arm and a biplane system if it uses two arms. Biplane systems provide two X-ray images which enable better 3-D imaging and real-time navigation. Most of X-ray imaging systems include an X-ray source, an image intensifier and a recording medium for each X-ray imaging arm.

One concern today is to prevent scattered X-rays from reaching the image intensifier during interventional procedures because the scattered X-rays may present a health concern for medical personnel who are in the operation room performing the procedures. The concern can be addressed by using a collimator to collimate the X-ray beam to a region of interest for imaging the target of interest.

For most interventional procedures, correct setting of the collimation and the region of interest (ROI)-filter position can reduce unnecessary X-ray radiation to the medical staff. In some diagnostic procedures, the collimator is adjusted to optimally cover parts of the scene where there is no body part. However, in some interventional procedures the collimator is adjusted to cover some body parts which are not of interest to the physicians. The ROI-filter may be positioned so that regions surrounding the ROI are imaged with attenuated radiation, resulting in a less intense and noisier fluoroscopic image. In many X-ray procedures, such an atrial fibrillation ablation procedure, contrast media is injected into a patient and is captured with the X-ray imaging device.

There are at least two characteristics of the interventional procedures which utilize X-ray imaging equipment.

Figure 1:
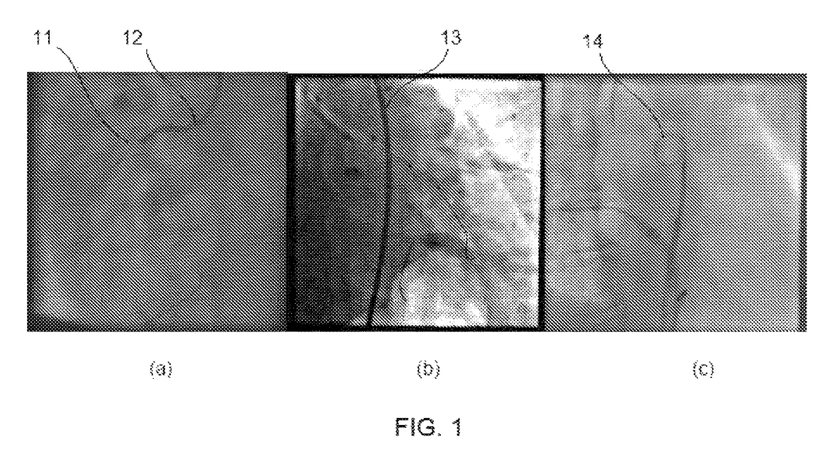
FIGS. 1(a)-(c) show X-ray images of various interventional procedures in which different interventional devices are employed, according to embodiments of the disclosure.

1. In most interventional procedures, various medical devices are inserted and guided to the area of interest inside the patient or subject during the procedure. Most of time these medical devices are in clearly visible areas of the X-ray images. FIGS. 1(a)-(c) show X-ray images of various interventional procedures in which different interventional devices are employed, such as a stent 11, a guiding catheter 12 and a guidewire 13 in FIGS. 1(a) and (b), and different catheters and a cryo-balloon catheter 14 in FIG. 1(c). The collimator and ROI-filter should be set so that the region of imaging covers the medical devices and relevant structures of the patient. The optimal collimation settings depend on the locations of these devices in addition to the subject's structures of interest. Such interventional medical devices include:
   a. a catheter,
   b. a temperature probe,
   c. a guidewire,
   d. a stent,
   e. a needle
   f. an Intravascular ultrasound (IVUS) transducer,
   g. an intra-cardiac echocardiography (ICE) catheter,
   h. a Trans-esophageal echocardiography (TEE) probe, etc.

2. The settings of the collimator and ROI-filter need to be changed whenever there is a new device or as the procedure requires. It can happen in many cases. For example, the collimator may need to be updated when the following scenarios happen: a contrast medium is injected, the interventional device(s) moves to a new location inside the collimation, or a new interventional device(s) is removed from the procedure. Manually setting the collimator and the ROI-filter whenever there is a need minimizes the radiation exposure to the medical staff, however, demands much human effort and increases the duration of the procedures. Another solution could use an eye-tracker, which however is insufficiently mature for use in clinical procedures.

SUMMARY

Exemplary embodiments of the disclosure as described herein generally include systems and methods for real-time collimation and ROI-filter positioning in X-ray imaging in interventional procedures.

According to an embodiment of the disclosure, there is provided a method for real-time collimation and ROI-filter positioning in X-ray imaging in interventional procedures, including acquiring an image of a region-of-interest (ROI) at a beginning of a medical intervention procedure on a subject, classifying the image based on low-level features in the image to determine a type of procedure being performed, determining a list of landmarks in the image from the type of procedure being performed, and loading a pre-trained landmark model for each landmark in the list of landmarks, where landmarks include anatomical structures of the subject and medical devices being used in the medical intervention procedure, and computing collimator settings of an X-ray imaging device from ROI filter margins and bounding boxes of the landmarks calculated using the landmark models.

According to a further embodiment of the disclosure, the method includes presenting to an operator the computed collimator settings of the X-ray imaging device, and receiving a confirmation of the operator the computed collimator settings from the operator.

According to a further embodiment of the disclosure, the method includes, during the medical intervention procedure, detecting that a landmark has moved into the ROI, and recomputing the ROI filter margins and the collimator settings of the X-ray imaging device.

According to a further embodiment of the disclosure, the landmark models are used to detect landmarks in the image.

According to a further embodiment of the disclosure, the landmarks include balloon markers, guiding catheters, guidewires, intravascular ultrasound transducers, vessels, ablation catheter electrodes, circumferential mapping catheter electrodes, coronary sinus catheter electrodes, calcium, and bone structures.

According to a further embodiment of the disclosure, if no pre-trained landmark model exits for a landmark, the method further comprises initializing the landmark, receiving positive samples of the landmark from a user, receiving negative samples of the landmark from other regions of the image, determining an appearance of the image from an image patch that represents an appearance of the initialized landmark, and training a landmark model using the positive samples, the negative samples, and the image appearance.

According to a further embodiment of the disclosure, the landmark is initialized with one of a line segment, a curve, a bounding box, a circle or other similar types of structures.

According to a further embodiment of the disclosure, the low-level features include edges, Haar-like features, scale-invariant features, histogram of ordered gradients, and local ternary patterns (LTP).

According to a further embodiment of the disclosure, the image is classified by a classifier based on the type of procedure being performed, where the procedure types include an electrophysiology procedure, an intravascular ultrasound procedure, a chronic total occlusion (CTO) procedure, and a balloon angioplasty procedure.

According to a another embodiment of the disclosure, there is provided a method for real-time collimation and ROI-filter positioning in X-ray imaging in interventional procedures, including acquiring an image of a region-of-interest (ROI) at a beginning of a medical intervention procedure on a subject, classifying the image based on a type of procedure being performed, detecting landmarks in the image, where the landmarks being detected are determined from the type of procedure being performed, where landmarks include anatomical structures of the subject and medical devices being used in the medical intervention procedure, and computing collimator settings of an X-ray imaging device from ROI filter margins and bounding boxes of the landmarks calculated using the detected landmarks.

According to a further embodiment of the disclosure, the method includes determining a list of landmarks from the type of procedure being performed and loading a pre-trained landmark model for each landmark in the list of landmarks, where the landmark models are used to detect landmarks in the image.

According to a further embodiment of the disclosure, if no pre-trained landmark model exits for a landmark, the method further comprises initializing the landmark, receiving positive samples of the landmark from a user, receiving negative samples of the landmark from other regions of the image, determining an appearance of the image from an image patch that represents an appearance of the initialized landmark, and training a landmark model using the positive samples, the negative samples, and the image appearance.

According to a further embodiment of the disclosure, the method includes presenting to an operator the computed collimator settings of the X-ray imaging device, and receiving a confirmation of the operator the computed collimator settings from the operator.

According to a further embodiment of the disclosure, the method includes, during the medical intervention procedure, detecting that a landmark has moved into the ROI, and recomputing the ROI filter margins and the collimator settings of the X-ray imaging device.

According to a further embodiment of the disclosure, the image is classified using low-level features, where the low-level features include edges, Haar-like features, scale-invariant features, histogram of ordered gradients, and local ternary patterns (LTPs).

According to a another embodiment of the disclosure, there is provided a non-transitory program storage device readable by a computer, tangibly embodying a program of instructions executed by the computer to perform the method steps for real-time collimation and ROI-filter positioning in X-ray imaging in interventional procedures.

DETAILED DESCRIPTION OF EXEMPLARY EMBODIMENTS

Exemplary embodiments of the disclosure as described herein generally include systems and methods for real-time collimation and ROI-filter positioning in X-ray imaging in interventional procedures. Accordingly, while the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the disclosure are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Embodiments of the present disclosure can provide methods for automatically setting a collimator and an ROI-filter in an optimal way and in real time to minimize scattered X-rays by taking into account the aforementioned characteristics. Methods according to embodiments of the disclosure can classify a scene into different categories based on the presence of medical devices or structures in the fluoroscopic images. According to embodiments of the disclosure, structures of the subject and the medical devices used in the procedure are referred to as "landmarks". Based on the detected scene category, models of the corresponding landmarks can be loaded to detect the locations of the landmarks in the image and to generate the collimator and ROI-filter settings. For example, if an atrial fibrillation procedure is detected, models of the ablation catheter, the coronary sinus catheter and the circumferential mapping catheter are automatically loaded. If models do not exist for a landmark, the landmark is considered to be new, and a "tag and learn" method is used to allow a technician to initialize the landmark, and then to detect similar landmarks in the X-ray image. The detected new landmarks are added to a landmark database.

Figure 2:
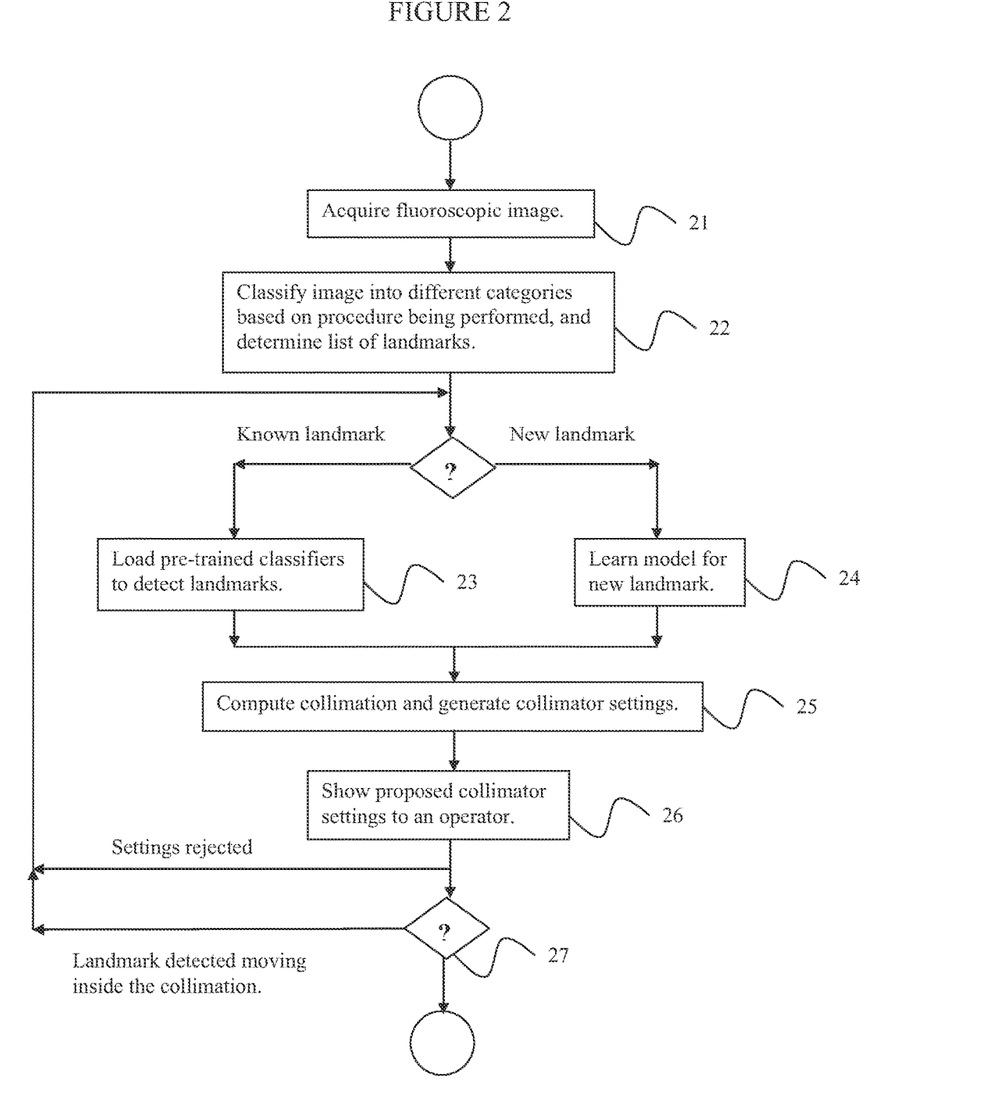
FIG. 2 is a flowchart of a method for real-time collimation and ROI-filter positioning in X-ray imaging in interventional procedures, according to embodiments of the disclosure.

FIG. 2 is a flowchart of an exemplary, non-limiting method for real-time collimation and ROI-filter positioning in X-ray imaging in interventional procedures via automatic detection and tracking the landmarks of interest. Referring now to the figure, a method starts at step 21 by acquiring a fluoroscopic image. The image is a monoplane image if the fluoroscopic imaging system is a monoplane system or a biplane frame otherwise. The image is acquired at the beginning of a procedure and includes the medical devices at the time, and after the X-ray imaging device has been centered at the region of interest of the patient or subject.

After an initial image is captured, the image or scene can be classified at step 22 into different categories based on the procedure being performed, since different medical procedures employ different medical devices and the fluoroscopic images have different regions of interest in the patient body. According to embodiments of the disclosure, the scene categorization uses low level image features, such as edges, Haar-like features, scale-invariant features, histograms of ordered gradients, local ternary patterns (LTP), etc., and employs a classifier to classify the scene. An exemplary, non-limiting list of interventional procedures for classifying an image includes an electrophysiology procedure, an intravascular ultrasound procedure, a chronic total occlusion (CTO) procedure, a balloon angioplasty procedure, etc.

Once a scene is determined, it can be determined which landmarks to look for, and pre-trained classifiers can be loaded at step 23 to detect those landmarks. The determination of which landmarks are present in the image can be performed manually by an operator, or automatically. In manual mode, an operator examines the image and selects a list of landmarks from a list of candidate landmarks. Alternatively, in an automatic mode, all pre-trained landmark models are loaded to detect the presence of the landmarks in the image, from which a list of landmark models is selected. The pre-trained landmark models are landmark specific and are learned from a large number of annotated X-ray images. An exemplary, non-limiting list of pre-trained models for the following landmarks is as follows:

Balloon markers which are usually present in the stent procedures;
Guiding catheter which are usually present in the IVUS procedures;
Guidewires which are also present in the IVUS and many other procedures;
IVUS transducer;
Vessels which are visible after contrast injection;
Ablation catheter electrodes which are present in ablation EP procedures;
Circumferential mapping catheter electrodes which are also present in the ablation EP procedures;
Coronary sinus catheter electrodes, used in EP procedures;
Calcium which are present in some interventional procedures; and
Bone structures.

Figure 3:
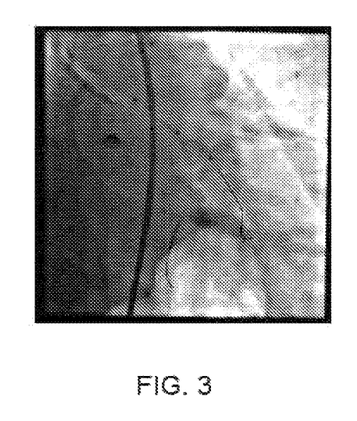
FIG. 3 shows a stenting procedure, according to embodiments of the disclosure.

As an example, in the case of a stenting procedure, an image of which is shown in FIG. 3, models of the following landmarks are selected: (1) the guiding catheter; (2) the balloon markers; and (3) the guidewire. The list of landmark models can be stored in a database.

Exemplary, non-limiting algorithms according to embodiments of the disclosure for detecting these three landmarks are as follows.

Figure 4:
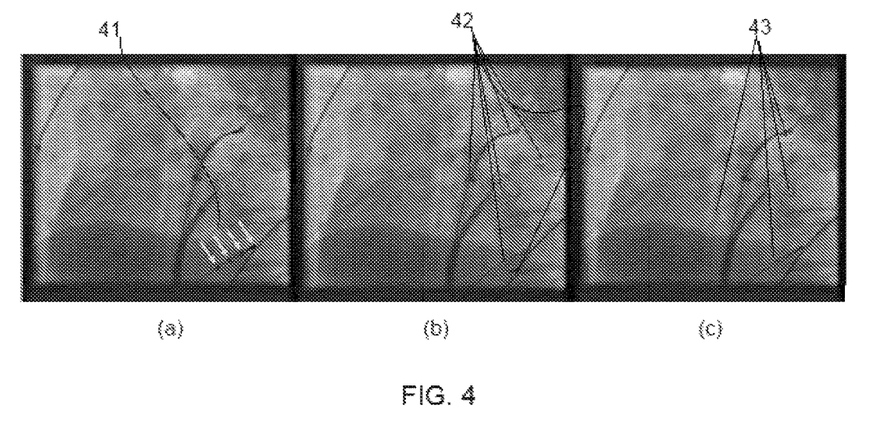
FIGS. 4(a)-(c) illustrate the detection of electrodes on a coronary sinus catheter, according to embodiments of the disclosure.

FIGS. 4(a)-(c) illustrate the detection of electrodes on a coronary sinus catheter. In FIG. 4(a), arrows 41 indicate the electrodes; in FIG. 4(b), points 42 are on the candidate electrode locations; and FIG. 4(c) shows the detected candidate locations 43 after non max suppression. The catheter tip and electrodes can be detected as oriented points $(x, y, \theta)$, and can be parameterized by their position $(x, y)$ and orientation $(\theta)$. For fast detection, Marginal Space Learning can be used to first detect just the tip and electrode positions $(x, y)$ and then at promising positions search for all orientations $(\theta)$. The tip and electrode positions $(x, y)$ can be detected using trained binary classifiers. Exemplary, non-limiting classifiers use about 100,000 Haar features in a centered window of size $(k \times k)$. An exemplary, non-limiting classifier is a Probabilistic Boosting Tree (PBT) that can output a probability $P(e=(x, y)|D)$, where D is the set of features. The catheter tip is different from other electrodes in term of context and appearance and it can be detected more reliably than other electrodes. The detected electrode and candidate positions are then augmented with a set of discrete orientations and provided to a trained oriented point detector, and the same applies for the detected tip positions. Exemplary oriented point detectors use a richer feature pool, including steerable feature responses and image intensity differences relative to the query position and orientation. The set of detected electrodes and tips at each frame is provided to a non-maximal suppression (NMS) stage that selects the clustered detections. In each frame, at most K electrodes and F tips are selected.

Figure 5:
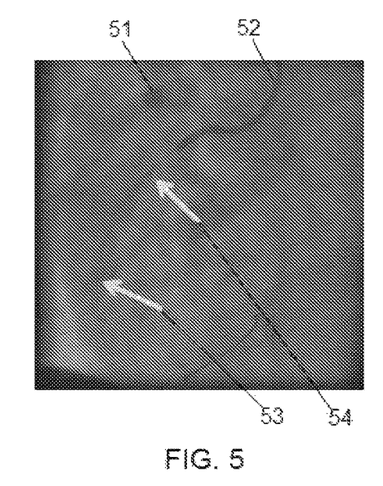
FIG. 5 is an X-ray image of balloon markers, a guidewire, a stent and a guiding catheter, according to embodiments of the disclosure.

Similar to the detection of catheter electrodes, a balloon marker detection according to embodiments of the disclosure includes two steps. In a first step, a PBT classifier detects the candidate marker locations, while in a second step, a pair of two candidate markers is evaluated by another PBT classifier. FIG. 5 is an X-ray image of balloon markers 51, a guidewire 52, a stent 53 and a guiding catheter 54.

An exemplary, non-limiting detection algorithm according an embodiment of the disclosure of the guidewire includes a semantic guidewire model that contains three parts, including a catheter tip, a guidewire tip and a guidewire body. Detection of these different parts are integrated into a Bayesian formula for detection of the whole guidewire. A hierarchical and multi-resolution scheme is applied to efficiently detect the guidewires.

Landmark detection according to embodiments of the disclosure can be performed in parallel when no other computation workloads, such as visualization and GUI interaction, are required.

Figure 6:
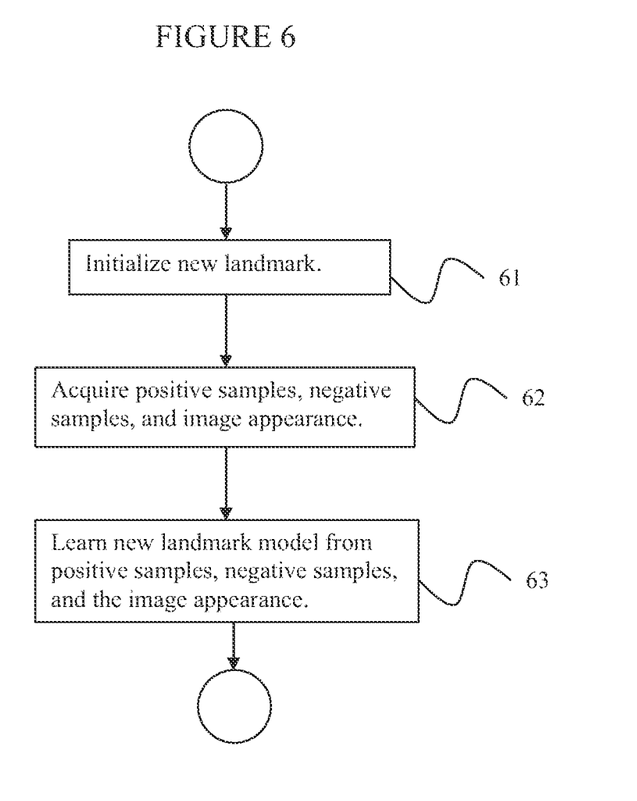
FIG. 6 is a flow chart of a tag-and-learn method according to an embodiment of the disclosure.

Referring again to FIG. 2, for a new type of landmark, such as a new medical device or a hard-to-define pattern, such as a calcification, for which a pre-trained model is not available, according to an embodiment of the disclosure, a tag-and-learn method can be used at step 24 to learn the model online from user initialization. A flow chart of a tag-and-learn method according to an embodiment of the disclosure is shown in FIG. 6. Referring to FIG. 6, a new landmark can be initialized manually or semi-automatically by the operator at step 61. Exemplary, non-liming initializations include a line segment, a curve, a bounding box, a circle or other similar types of structures. At step 62, examples of positive samples are provided by user initialization, negative samples are acquired from the remaining regions of the image, and an image appearance is acquired by learning a template of the initialized landmark, where a template is an image patch which represents the appearance of the landmark. For example a template matching based approach can be used in a patent application which can track a coronary sinus catheter in X-ray images in an atrial fibrillation ablation procedure. The learning of the new landmark model is performed at step 63 by utilizing the positive samples, the negative samples, and the image appearance.

Referring again to FIG. 2, the collimation is computed and the collimator settings are generated at step 25. Bounding boxes (B_left, B_right, B_top, B_bottom) of all landmarks are computed from the landmark models, along with margins (M_left, M_right, M_top, M_bottom) of the ROI-filter. From these, the collimator settings, (C_left, C_right, C_top, C_bottom) can be generated. According to embodiments of the disclosure, the bounding boxes and ROI-filter margins can be determined automatically based on what type of landmark is important in a given scene. For example, for a stent implantation scene, then the location of the two balloon markers are important and the images should define an ROI around this pair of balloon markers. Exemplary, non-limiting collimator settings are $C\_left=\max(0, B\_left-M\_left),$ $C\_right=\min(image\_columns, B\_right+M\_right),$ $C\_top=\max(0, B\_top-M\_top),$ $C\_bottom=\min(image\_rows, B\_bottom+M\_bottom),$ where it is assumed that the collimator settings define a rectangle. According to other embodiments of the disclosure, if the collimator has another shape, such as a circle, the collimator's setting can be derived similar to the above case. At step 26, the proposed collimator settings are shown to an operator to confirm. The operator can accept these new settings to set the collimator, or reject the settings to update them.

A system according to an embodiment of the disclosure can track landmarks of interest when one or more landmarks move into the collimation area. At step 27, if a landmark of interest is detected as moving inside the collimation, the collimator and ROI filter settings are re-computed and shown to the operator for confirmation using the above steps 22-26.

A method according to an embodiment of the disclosure can work automatically in real time with little or no human input except during system initialization and confirmation of the updated collimator and ROI-filter settings, however, an operator can manually set these parameters at any time.

It is to be understood that embodiments of the present disclosure can be implemented in various forms of hardware, software, firmware, special purpose processes, or a combination thereof. In one embodiment, an embodiment of the present disclosure can be implemented in software as an application program tangible embodied on a computer readable program storage device. The application program can be uploaded to, and executed by, a machine comprising any suitable architecture.

Figure 7:
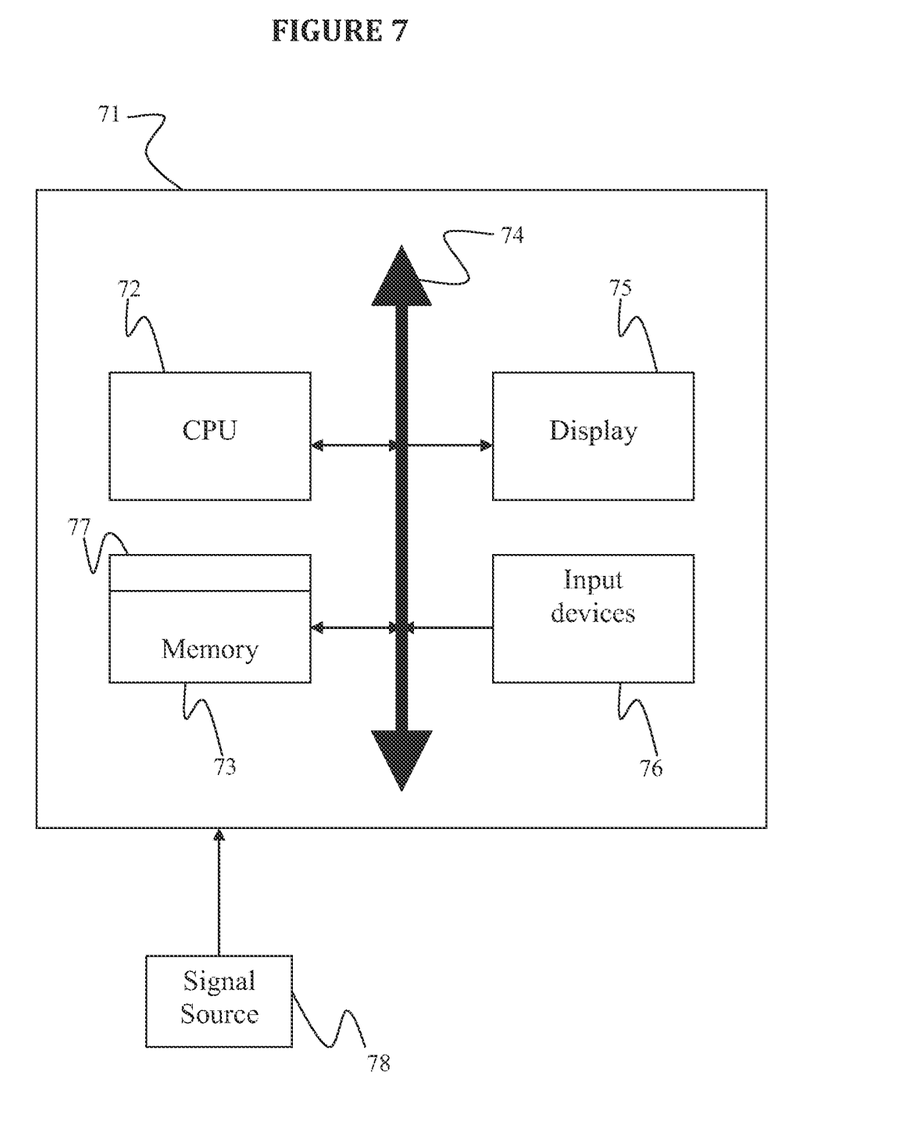
FIG. 7 is a block diagram of an exemplary computer system for real-time collimation and ROI-filter positioning in X-ray imaging in interventional procedures, according to an embodiment of the disclosure.

FIG. 7 is a block diagram of an exemplary computer system for implementing a method for real-time collimation and ROI-filter positioning in X-ray imaging in interventional procedures according to an embodiment of the disclosure. Referring now to FIG. 7, a computer system 71 for implementing an embodiment of the present disclosure can comprise, inter alia, a central processing unit (CPU) 72, a memory 73 and an input/output (I/O) interface 74. The computer system 71 is generally coupled through the I/O interface 74 to a display 75 and various input devices 76 such as a mouse and a keyboard. The support circuits can include circuits such as cache, power supplies, clock circuits, and a communication bus. The memory 73 can include random access memory (RAM), read only memory (ROM), disk drive, tape drive, etc., or a combinations thereof. Embodiments of the present disclosure can be implemented as a routine 77 that is stored in memory 73 and executed by the CPU 72 to process the signal from the signal source 78. As such, the computer system 71 is a general purpose computer system that becomes a specific purpose computer system when executing the routine 77 of the present disclosure.

The computer system 71 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which an embodiment of the present disclosure is programmed. Given the teachings of the present disclosure provided herein, one of ordinary skill in the related art will be able to contemplate these and similar implementations or configurations of the present disclosure.

While embodiments of the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A method for real-time collimation and ROI-filter positioning in X-ray imaging in interventional procedures, comprising the steps of:
   acquiring an image of a region-of-interest (ROI) at a beginning of a medical intervention procedure on a subject;
   classifying the image based on low-level features in the image to determine a type of procedure being performed;
   determining a list of landmarks in the image from the type of procedure being performed, and loading a pre-trained landmark model for each landmark in the list of landmarks, wherein landmarks include anatomical structures of the subject and medical devices being used in the medical intervention procedure; and
   computing collimator settings of an X-ray imaging device from ROI filter margins and bounding boxes of the landmarks calculated using the landmark models.

2. The method of claim 1, further comprising presenting to an operator the computed collimator settings of the X-ray imaging device, and receiving a confirmation of the operator the computed collimator settings from the operator.

3. The method of claim 1, further comprising, during the medical intervention procedure, detecting that a landmark has moved into the ROI, and recomputing the ROI filter margins and the collimator settings of the X-ray imaging device.

4. The method of claim 1, wherein the landmark models are used to detect landmarks in the image.

5. The method of claim 4, wherein landmarks include balloon markers, guiding catheters, guidewires, intravascular ultrasound transducers, vessels, ablation catheter electrodes, circumferential mapping catheter electrodes, coronary sinus catheter electrodes, calcium, and bone structures.

6. The method of claim 4, wherein if no pre-trained landmark model exits for a landmark, the method further comprises initializing the landmark, receiving positive samples of the landmark from a user, receiving negative samples of the landmark from other regions of the image, determining an appearance of the image from an image patch that represents an appearance of the initialized landmark, and training a landmark model using the positive samples, the negative samples, and the image appearance.

7. The method of claim 6, wherein the landmark is initialized with one of a line segment, a curve, a bounding box, a circle or other similar types of structures.

8. The method of claim 1, wherein the low-level features include edges, Haar-like features, scale-invariant features, histogram of ordered gradients, and local ternary patterns (LTP).

9. The method of claim 1, wherein the image is classified by a classifier based on the type of procedure being performed, wherein the procedure types include an electrophysiology procedure, an intravascular ultrasound procedure, a chronic total occlusion (CTO) procedure, and a balloon angioplasty procedure.

10. A method for real-time collimation and ROI-filter positioning in X-ray imaging in interventional procedures, comprising the steps of:
    acquiring an image of a region-of-interest (ROI) at a beginning of a medical intervention procedure on a subject;
    classifying the image based on a type of procedure being performed;
    detecting landmarks in the image, wherein the landmarks being detected are determined from the type of procedure being performed, wherein landmarks include anatomical structures of the subject and medical devices being used in the medical intervention procedure; and
    computing collimator settings of an X-ray imaging device from ROI filter margins and bounding boxes of the landmarks calculated using the detected landmarks.

11. The method of claim 10, further comprising determining a list of landmarks from the type of procedure being performed and loading a pre-trained landmark model for each landmark in the list of landmarks, wherein the landmark models are used to detect landmarks in the image.

12. The method of claim 11, wherein if no pre-trained landmark model exits for a landmark, the method further comprises initializing the landmark, receiving positive samples of the landmark from a user, receiving negative samples of the landmark from other regions of the image, determining an appearance of the image from an image patch that represents an appearance of the initialized landmark, and training a landmark model using the positive samples, the negative samples, and the image appearance.

13. The method of claim 10, further comprising presenting to an operator the computed collimator settings of the X-ray imaging device, and receiving a confirmation of the operator the computed collimator settings from the operator.

14. The method of claim 10, further comprising, during the medical intervention procedure, detecting that a landmark has moved into the ROI, and recomputing the ROI filter margins and the collimator settings of the X-ray imaging device.

15. The method of claim 10, wherein the image is classified using low-level features, wherein the low-level features include edges, Haar-like features, scale-invariant features, histogram of ordered gradients, and local ternary patterns (LTPs).

16. A non-transitory program storage device readable by a computer, tangibly embodying a program of instructions executed by the computer to perform the method steps for real-time collimation and ROI-filter positioning in X-ray imaging in interventional procedures, the method comprising the steps of:
    acquiring an image of a region-of-interest (ROI) at a beginning of a medical intervention procedure on a subject;
    classifying the image based on low-level features in the image to determine a type of procedure being performed;
    determining a list of landmarks in the image from the type of procedure being performed, and loading a pre-trained landmark model for each landmark in the list of landmarks, wherein landmarks include anatomical structures of the subject and medical devices being used in the medical intervention procedure; and
    computing collimator settings of an X-ray imaging device from ROI filter margins and bounding boxes of the landmarks calculated using the landmark models.

17. The computer readable program storage device of claim 16, the method further comprising presenting to an operator the computed collimator settings of the X-ray imaging device, and receiving a confirmation of the operator the computed collimator settings from the operator.

18. The computer readable program storage device of claim 16, the method further comprising, during the medical intervention procedure, detecting that a landmark has moved into the ROI, and recomputing the ROI filter margins and the collimator settings of the X-ray imaging device.

19. The computer readable program storage device of claim 16, wherein the landmark models are used to detect landmarks in the image.

20. The computer readable program storage device of claim 19, wherein landmarks include balloon markers, guiding catheters, guidewires, intravascular ultrasound transducers, vessels, ablation catheter electrodes, circumferential mapping catheter electrodes, coronary sinus catheter electrodes, calcium, and bone structures.

21. The computer readable program storage device of claim 19, wherein if no pre-trained landmark model exits for a landmark, the method further comprises initializing the landmark, receiving positive samples of the landmark from a user, receiving negative samples of the landmark from other regions of the image, determining an appearance of the image from an image patch that represents an appearance of the initialized landmark, and training a landmark model using the positive samples, the negative samples, and the image appearance.

22. The computer readable program storage device of claim 21, wherein the landmark is initialized with one of a line segment, a curve, a bounding box, a circle or other similar types of structures.

23. The computer readable program storage device of claim 16, wherein the low-level features include edges, Haar-like features, scale-invariant features, histogram of ordered gradients, and local ternary patterns (LTP).

24. The computer readable program storage device of claim 16, wherein the image is classified by a classifier based on the type of procedure being performed, wherein the procedure types include an electrophysiology procedure, an intravascular ultrasound procedure, a chronic total occlusion (CTO) procedure, and a balloon angioplasty procedure.

* * * * *